(12) United States Patent
Kalisek

(10) Patent No.: US 8,326,432 B2
(45) Date of Patent: Dec. 4, 2012

(54) FOOT DROP DEVICE STORAGE POLE

(76) Inventor: Rod S. Kalisek, Gretna, NE (US)

( * ) Notice: Subject to any disclaimer, the term of this patent is extended or adjusted under 35 U.S.C. 154(b) by 275 days.

(21) Appl. No.: 12/804,280

(22) Filed: Jul. 19, 2010

(65) Prior Publication Data

US 2012/0012486 A1 Jan. 19, 2012

(51) Int. Cl.
*A61N 1/36* (2006.01)

(52) U.S. Cl. .......................................... 607/49; 206/438

(58) Field of Classification Search ........................ None
See application file for complete search history.

(56) References Cited

U.S. PATENT DOCUMENTS

| | | | | |
|---|---|---|---|---|
| 21,620 | A * | 9/1858 | Nevins et al. ................. | 432/155 |
| 3,354,576 | A * | 11/1967 | Gralnick ......................... | 446/76 |
| 4,037,428 | A * | 7/1977 | Giannotti ........................ | 62/371 |
| 4,045,068 | A * | 8/1977 | Nelson ......................... | 294/19.2 |
| 4,255,944 | A * | 3/1981 | Gardner et al. .............. | 62/457.8 |
| 5,181,515 | A * | 1/1993 | Negishi ......................... | 600/485 |
| 5,269,156 | A * | 12/1993 | van de Velde et al. ....... | 62/457.4 |
| 5,427,246 | A * | 6/1995 | Hadjikhani ................... | 206/554 |
| 5,639,055 | A * | 6/1997 | Fritz .............................. | 248/519 |
| 5,738,122 | A * | 4/1998 | Armbruster et al. .......... | 132/290 |
| D417,614 | S * | 12/1999 | Chu ............................... | D9/504 |
| 6,050,401 | A * | 4/2000 | Michaelson ................... | 206/225 |
| 6,062,131 | A * | 5/2000 | Holland ......................... | 99/345 |
| 6,119,585 | A * | 9/2000 | Guidry ........................... | 99/345 |
| 6,189,258 | B1 * | 2/2001 | Anderson ...................... | 43/54.1 |
| 6,298,871 | B1 * | 10/2001 | Pickens et al. ................ | 137/268 |
| 6,854,596 | B1 * | 2/2005 | Wiese ............................ | 206/225 |
| 6,968,955 | B2 * | 11/2005 | Steeber ......................... | 206/702 |
| 7,387,204 | B2 * | 6/2008 | Lee ................................ | 206/362 |
| 2003/0226865 | A1 * | 12/2003 | Haas .............................. | 223/68 |
| 2010/0163690 | A1 * | 7/2010 | Goetz ............................ | 248/89 |
| 2010/0181221 | A1 * | 7/2010 | Rivers, Jr. ..................... | 206/457 |

OTHER PUBLICATIONS

Bioness Inc., 25103 Rye Canyon Loop, Valencia, CA 91355, pp. 6-7 of brochure #926-00043; Retrieval date: Jun.29, 2010.
Bioness L300 FAQ, Web pages http://orthomedics.us/BionessFAQ.aspx, 3 pages, Jun. 29, 2010.
Bioness/Walkaide, Web pages http://orthomedics.us/FES.aspx, 2 pages, Jun. 29, 2010.
Walkaide, web page http://orthomedics.us/walkaide.aspx, 1 page, Jun. 29, 2010.

* cited by examiner

*Primary Examiner* — Kennedy Schaetzle
(74) *Attorney, Agent, or Firm* — Dennis L. Thomte; Thomte Patent Law Office LLC

(57) ABSTRACT

A storage and support device for storing and supporting components of a Functional Electrical Stimulator Foot Drop Device is disclosed and includes an upstanding hollow tubular member extending upwardly from a base portion. The interior of the tubular member may be used to store certain of the components of the foot drop device, other than the leg cuff portion thereof, during periods of non-use. The leg cuff portion of the foot drop device is wrapped around the tubular member with the tubular member having an exterior curved surface which corresponds to the shape to the disc-shaped electrodes at the inner surface of the leg cuff so that a plastic sheet covering the electrodes will be maintained in intimate contact with the electrodes to extend the life thereof.

3 Claims, 3 Drawing Sheets

FOOT DROP DEVICE STORAGE POLE

BACKGROUND OF THE INVENTION

1. Field of the Invention

This invention relates to a storage and support pole for use with a foot drop device such as a Functional Electrical Stimulator Foot Drop Device. More particularly, this invention relates to a storage and support pole wherein certain of the components of the foot drop device may be stored within the pole when the device is not in use and wherein the leg cuff of the foot drop device may be wrapped around the pole in a manner so that a plastic sheet covering the electrodes at the inner side of the leg cuff will be maintained in intimate contact with the electrodes to extend the usable life thereof.

2. Description of the Related Art

Millions of people are affected by foot drop, either directly or indirectly. Foot drop is a condition where the muscles in the foot are too weak to properly lift the foot and toes while walking. Foot drop is often present in persons who have conditions such as stroke, traumatic brain injury, incomplete spinal cord injury, multiple sclerosis and cerebral palsy. Functional Electrical Stimulation devices have been provided to stop the toes from dragging. Functional Electrical Stimulators are neuroprosthetic devices that bypass the brain's communication to the leg and tell the muscles to contract which lifts the foot and allows a more natural gait.

A popular foot drop system is that manufactured by Bioness, Inc. of Valencia, Calif. and identified as a Ness L300. The Ness L300, as well as other available foot drop devices, such as the Walkaide System, normally comprises a leg cuff which is wrapped around the leg of the person with the leg cuff having one or more flexible disc-shaped electrodes positioned at the inner side thereof which are electrically connected to a stimulation unit mounted on the exterior surface of the leg cuff. The Ness L300 also includes a wireless gait sensor that is placed within the shoe as well as a portable hand-held control unit to conveniently turn the stimulator on or off. The Ness L300 also includes a recharging unit which must be used frequently and usually at night, to recharge the control unit and the stimulator unit.

When the system is not being used, it is recommended that the electrodes on the inner side of the leg cuff be wetted and then a plastic sheet, such as used to cover the electrodes during shipment, is placed over the electrodes to prevent the electrodes from drying out. Even though the wetted electrodes are covered with the plastic sheet, the electrodes last for only two or three weeks and must be replaced. Applicant believes that the plastic sheet, after being placed on the electrodes, does not maintain intimate contact with the electrodes thereby permitting the electrodes to dry out over a period of time.

SUMMARY OF THE INVENTION

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

A storage and support device for storing and supporting components of a Functional Electrical Stimulator Foot Drop Device is provided with the foot drop device including a gait sensor, a portable wireless controller, a battery recharger, a flexible stimulation leg cuff adapted to be wrapped around a person's leg with the leg cuff having inner and outer sides and with at least one and usually two flexible, disc-shaped electrodes positioned at the inner side thereof, together with a flexible plastic sheet for placement over the electrodes when the device is not being worn by the user.

The storage and support device of this invention comprises a base portion and an upstanding hollow tubular member. The tubular member has an upper end, a lower end, an outer surface and an inner surface. The lower end of the tubular member is fixed to the base portion and extends upwardly therefrom. A cap is selectively removably mounted on the upper end of the tubular member to permit the upper end of the tubular member to be selectively closed. The tubular member has a height and diameter sufficient to permit the gait sensor, wireless controller or battery recharger to be stored therein. The diameter of the tubular member is sized so that the flexible functional leg cuff may be wrapped around the tubular member and supported thereon when not worn by the person and so that the inner surface of the tubular member is complimentary to the shape of the electrodes to maintain the flexible plastic sheet in intimate contact with the electrodes. In the preferred embodiment, the diameter of the tubular member is approximately four inches.

It is therefore a principal object of the invention to provide a foot drop device storage pole.

A further object of the invention is to provide a storage and support device for storing and supporting components of a Functional Electrical Stimulator Foot Drop Device.

A further object of the invention is to provide a storage and support device of the type described wherein the device includes a hollow tubular member which is sized so as to have a curvature at its outer surface which is complimentary in shape to the electrodes on the inner surface of the leg cuff so that a plastic sheet covering the electrodes is placed into intimate contact with the electrodes to extend the life thereof.

A further object of the invention is to provide a foot drop storage device of the type described which is convenient to use and which is esthetically pleasing.

These and other objects will be apparent to those skilled in the art.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

DESCRIPTION OF THE PREFERRED EMBODIMENT

Figure 1:
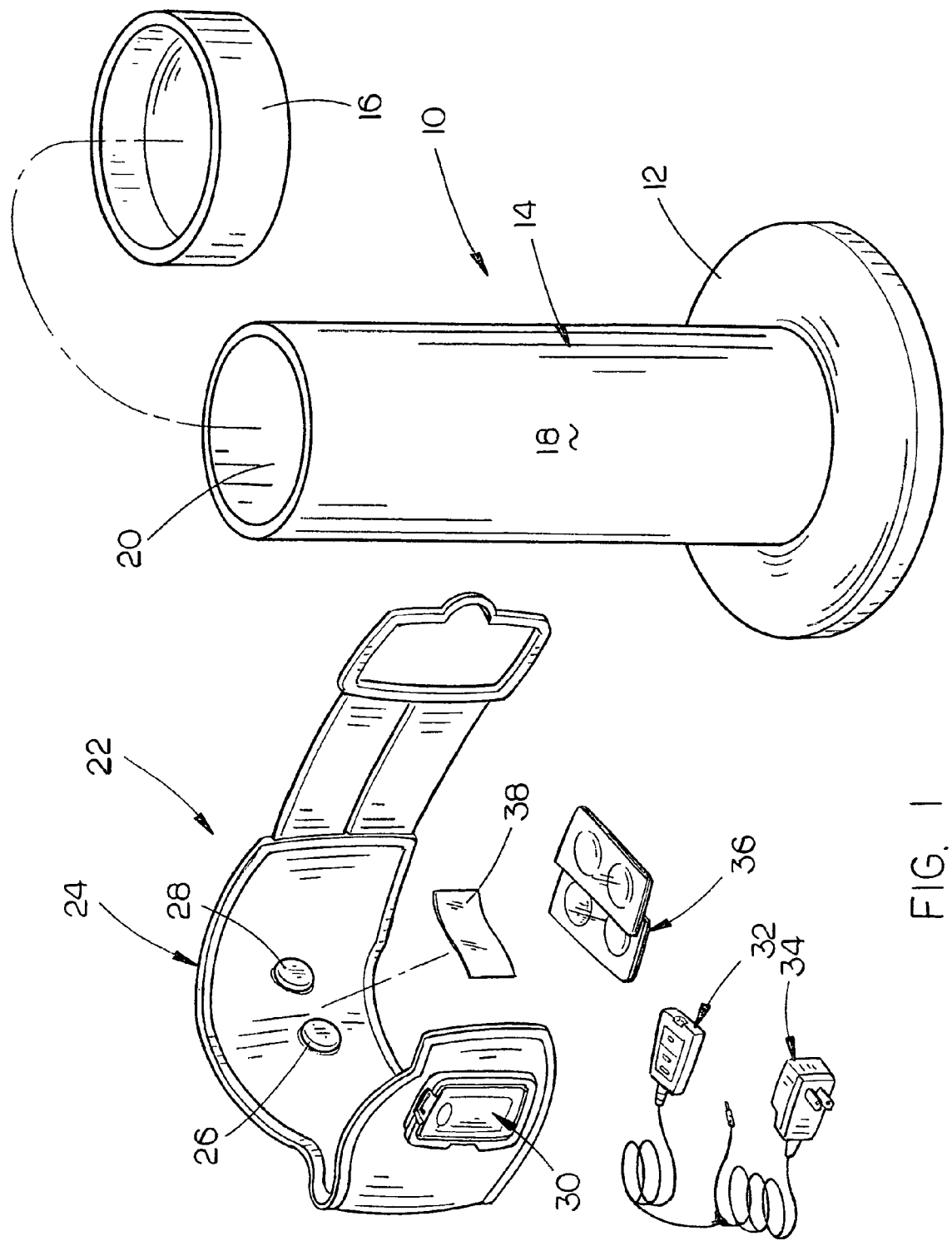
FIG. 1 is an exploded perspective view illustrating the storage and support device of this invention as well as a Functional Electrical Stimulator Foot Drop Device.

Embodiments are described more fully below with reference to the accompanying figures, which form a part hereof and show, by way of illustration, specific exemplary embodiments. These embodiments are disclosed in sufficient detail to enable those skilled in the art to practice the invention. However, embodiments may be implemented in many different forms and should not be construed as being limited to the embodiments set forth herein. The following detailed description is, therefore, not to be taken in a limiting sense in that the scope of the present invention is defined only by the appended claims.

The numeral 10 refers to the storage and support pole or device of this invention which includes a base 12 having a hollow tubular member 14 secured thereto and extending upwardly therefrom. Preferably, the diameter of the tubular member 14 is four inches with the base portion 12 having a diameter of approximately 12 inches. The device 10 also includes a cap 16 which may be positioned on the upper end of the tubular member 14 to close the same. For purposes of description, the tubular member 14 will be described as having an outer surface 18 and an interior compartment 20.

The numeral 22 refers to a Functional Electrical Stimulator Foot Drop Device such as manufactured by Ness or Walkaide. The device 22 includes a flexible leg cuff 24 having a pair of flexible disc-shaped electrodes 26 and 28 provided at the inner surface thereof. The electrodes are electrically connected to a stimulator device 30 which is battery operated. Device 22 also includes a portable wireless controller 32 and a recharger unit 34. Recharger unit 34 may be used to recharge the batteries in controller 32 and in the stimulation unit 30.

The electrodes normally come in a small packet such as seen in FIG. 1 and which is designated by the reference numeral 36. The electrodes within the packet 36 are covered by a flexible plastic sheet for shipment purposes and which is referred to by the reference numeral 38.

Figure 2:
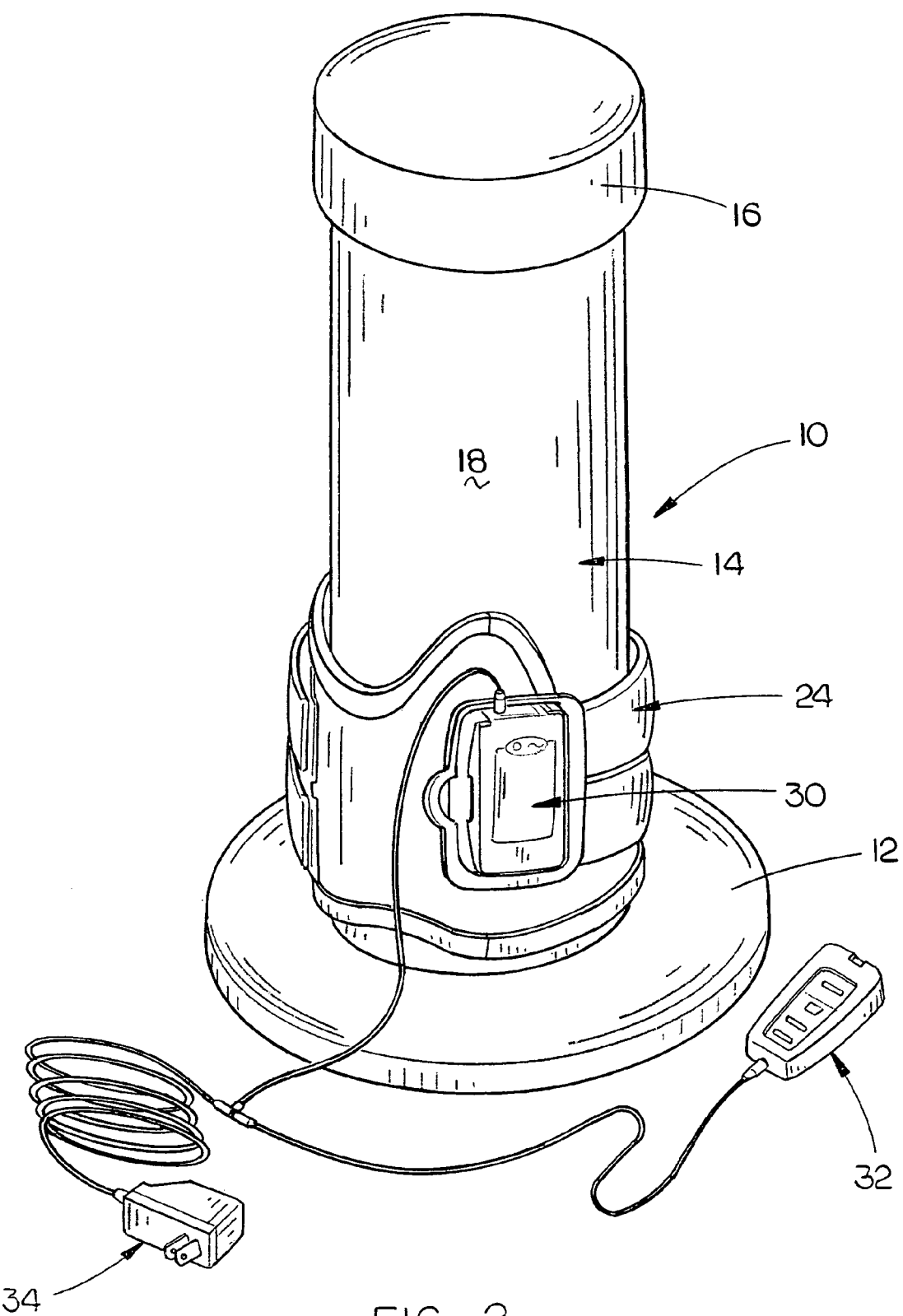
FIG. 2 is a perspective view illustrating the device of this invention having the leg cuff of the stimulator mounted thereon.
Figure 3:
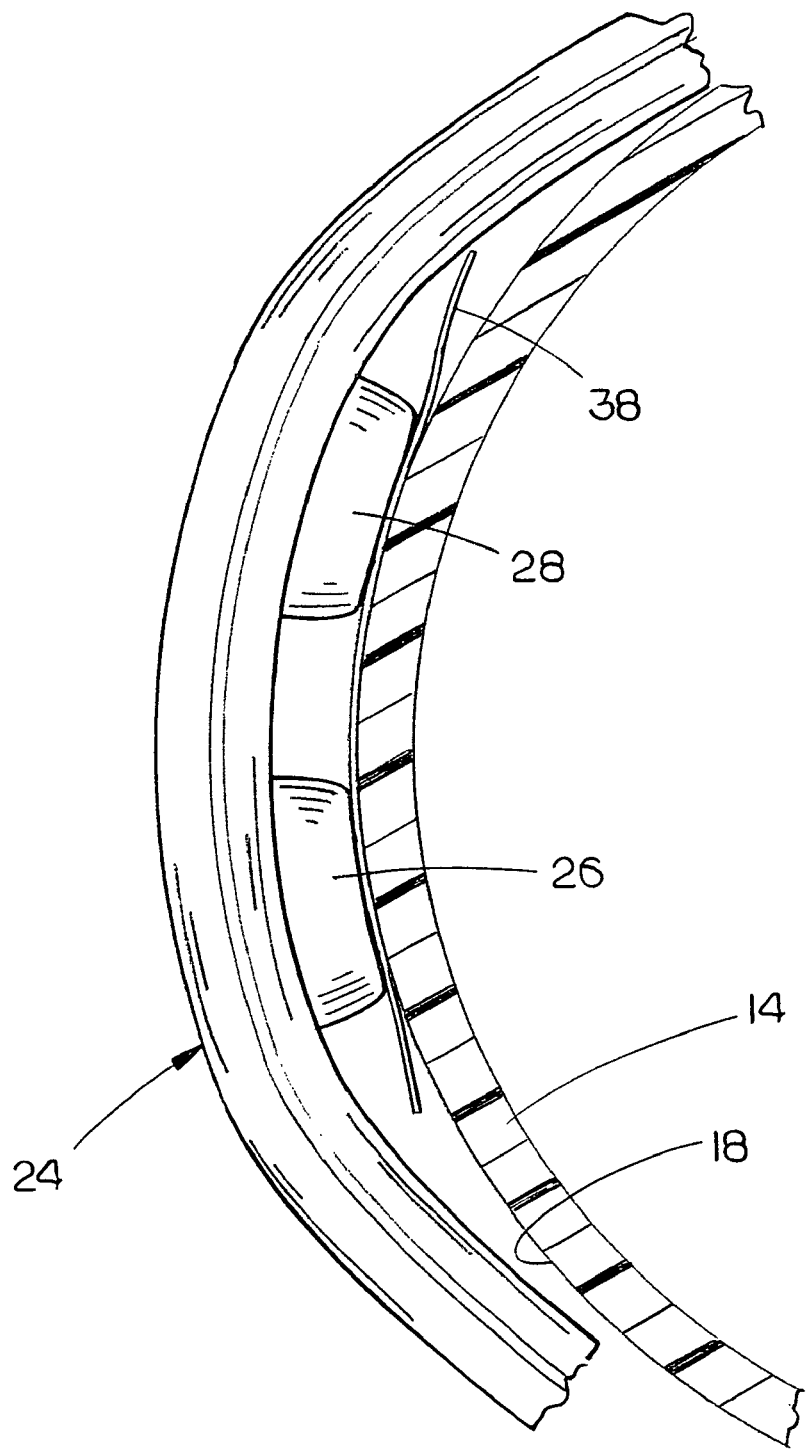
FIG. 3 is a partial sectional view illustrating the leg cuff wrapped around the support pole of the invention.

In the past, after the electrodes 26 and 28 have been secured to the inner surface of the leg cuff 24, the flexible sheet 38 is not discarded. When the leg cuff 24 is removed from the person's leg at night, the plastic sheet 38 is placed over the electrodes 26 and 28 after the electrodes have been wetted. The plastic sheet 38 prevents the electrodes 26 and 28 from drying out. Even with the use of the flexible sheet 38 during the times that the leg cuff 24 is not being worn, the life of the electrodes is perhaps only two to three weeks. It is for that purpose that Applicant has provided the storage and support device 10. When the leg cuff 26 is removed from the person, the electrodes 26 and 28 are wetted and the flexible sheet 38 is placed thereover. The leg cuff 24 is then wrapped around the tubular member 14 as seen in FIGS. 2 and 3. The outer surface 18 of the tubular member 24 is complimentary in shape to the flexible slightly curved electrodes 26 and 28 so that the flexible sheet 38 is maintained in intimate contact with the inner surfaces of the electrodes 26 and 28 thereby extending the life of the electrodes from the usual two to three weeks to at least eight weeks.

The stimulator unit 30 and the controller 32 may be recharged as seen in FIG. 2. The components of the device 10, other than the leg cuff 24, may be stored in the interior compartment 20 of the tubular member 14 during periods of non-use.

Thus it can be seen that the invention has accomplished all of its stated objectives.

Although the invention has been described in language that is specific to certain structures and methodological steps, it is to be understood that the invention defined in the appended claims is not necessarily limited to the specific structures and/or steps described. Rather, the specific aspects and steps are described as forms of implementing the claimed invention. Since many embodiments of the invention can be practiced without departing from the spirit and scope of the invention, the invention resides in the claims hereinafter appended.

The invention claimed is:

1. In combination:
   a Functional Electrical Stimulator Foot Drop Device including a gait sensor, a portable wireless controller, a battery recharger, a flexible functional stimulation leg cuff adapted to be wrapped around a person's leg having inner and outer sides with at least one flexible, disc-shaped electrode positioned at the inner side thereof, and a flexible plastic sheet for placement over the electrode when the device is not being used by the person, comprising:
   a storage and support device for said Functional Electrical Stimulator Foot Drop Device comprising a base portion; an upstanding hollow tubular member having an upper end, a lower end, an outer surface and an inner surface; said lower end of said tubular member being fixed to said base portion; a cap selectively removably mounted on said upper end of said tubular member; said tubular member having a height and diameter sufficient to permit the gait sensor, portable wireless controller or battery recharger to be stored therein; the diameter of said tubular member being sized so that the flexible functional leg stimulation cuff may be wrapped around said tubular member and supported thereon when not worn by the person and so that the outer surface of said tubular member is complimentary to the shape of the electrode to maintain the flexible plastic sheet in intimate contact with the electrode.

2. The combination of claim 1 wherein a pair of electrodes are provided at the inner surface of the cuff.

3. The combination of claim 1 wherein the diameter of said tubular member is approximately four inches.

* * * * *